United States Patent [19]

Ganguly et al.

[11] Patent Number: 4,743,598
[45] Date of Patent: May 10, 1988

[54] ANTIBACTERIAL 2-(AZACYCLOALKYL) PENEMS

[75] Inventors: Ashit K. Ganguly, Upper Montclair; Viyyoor M. Girijavallabhan, Parsippany; Adriano Afonso, West Caldwell; Jay Weinstein, Upper Montclair, all of N.J.

[73] Assignee: Schering Corporation, Kenilworth, N.J.

[21] Appl. No.: 446,928

[22] Filed: Dec. 6, 1982

[51] Int. Cl.$^4$ .................. A61K 31/43; C07D 499/00
[52] U.S. Cl. ..................................... 514/192; 540/310
[58] Field of Search ............... 260/245.2 R; 546/198; 424/267, 270; 514/192; 540/310

[56] References Cited

U.S. PATENT DOCUMENTS 4,271,172 6/1981 Rodriguez et al. .................. 514/193
4,386,030 5/1983 Christensen et al. ......... 260/245.2 R

OTHER PUBLICATIONS

Miller, G. et al., *Clinical Trials Journal*, 1980, 17, 6, 244–245.
Derwent Abstract of EP 70204, (published 1/19/83).

*Primary Examiner*—Richard A. Schwartz
*Attorney, Agent, or Firm*—Thomas D. Hoffman; Gerald S. Rosen

[57] ABSTRACT

Disclosed are 6-(1'hydroxyethyl)-2-(azacycloalkyl)-penem-3-carboxylic acids and salts or metabolizable esters thereof having an absolute stereochemistry of 5R,6S,8R. The compounds are useful and potent antibacterial agents and can be formulated into a variety of forms suitable for oral, parenteral or topical use.

12 Claims, No Drawings

ANTIBACTERIAL 2-(AZACYCLOALKYL) PENEMS

BACKGROUND OF THE INVENTION

There is a continuing need for new antibacterials since wide scale usage of any given antibacterial gives rise to resistant strains of pathogens. In addition, the known antibacterials suffer from the disadvantage of being effective only against certain types of microorganisms. Thus, new antibacterial agents are constantly being sought.

Antibacterials of the penem-type are known in the art. See, for instance, U.S. Pat. No. 4,301,074 (1982); U.S. Pat. No. 4,272,437 (1981) and U.S. Pat. No. 4,331,676 (1982).

DESCRIPTION OF THE INVENTION

This invention relates to novel 2-cycloiminoalkyl penems and to their use as antibacterial agents. More particularly, this invention concerns (5R,6S,8R)-6-(1'-hydroxyethyl)-2-(azacycloalkyl)penem-3-carboxylic acids and the pharmaceutically acceptable salts and metabolizable esters thereof of the formula

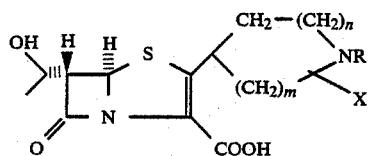

wherein
m is 0-2;
n is 1-3; and
X is a hydrogen, lower alkyl, lower alkoxy, amino, hydroxy, lower alkylthio, or carboxy group; R is hydrogen, lower alkyl, amidino or

wherein $R^1$ is hydrogen or $C_1$-$C_3$ alkyl; and the pharmaceutically acceptable salts and metabolizable esters thereof, in racemic or optically active form.

The lower alkyl groups referred to above contain 1-6 carbon atoms and include methyl, ethyl, propyl, butyl, pentyl, hexyl and the corresponding branched-chain isomers thereof. The lower alkoxy groups likewise contain 1-6, and preferably 1-3, carbon atoms and are illustrated by methoxy, ethoxy, n-propoxy, isopropoxy and the like.

The compounds of the present invention possess at least three asymetric carbon atoms, indicated in the partial formula below as the 5,6 and 8-position carbon atoms.

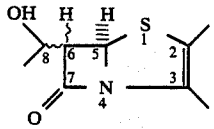

The configuration of these centers may be 5R,6R,8S or 5R,6S,8R. The preferred configuration for these carbon atoms is 5R,6S,8R. Additionally, depending upon the particular values for m, n and X, one or more asymetric carbon atom may exist in the 2-azacyclooalkyl substituent. The present invention is intended to include both the isomer mixtures and the individual separated and resolved isomers.

For the purposes of this invention, equivalent to the compounds of formula I are the alkali metal, alkaline-earth metal and amine salts. Examples of the alkali metal and alkaline-earth metal salts are the sodium, potassium, aluminum, magnesium and calcium salts. The amine salts may be formed from a wide variety of suitable organic amines, i.e., aliphatic, cycloaliphatic, primary, secondary or tertiary mono-, di- or polyamines, or heterocyclic bases. Specific examples are those salts derived from triethylamine, 2-hydroxyethylamine, di-(2-hydroxyethyl)amine, tri-(2-hydroxyethylaminoethyl ester) 1-ethylpiperidine, bicyclohexylamine, N,N'-dibenzylethylenediamine, pyridine, collidine, quinoline, procaine, dibenzylamine, N-benzyl-beta-phenethylamine, 1-ephenamine and N-alkylpiperidine. The compounds containing an acid group and a basic group can also be in the form of an inner salt, i.e., a Zwitterion.

The metabolizable esters are the physiologically cleavable esters, i.e., those esters known in the penicillin, cephalosporin and penem arts to be easily cleaved within the body to the parent acid. Examples of such metabolizable esters are those such a indanyl, phthalidyl, methoxymethyl, glycyloxymethyl, phenylglycyloxymethyl, thienylglycoloxymethyl or acyloxymethyl of the formula

wherein Y' is lower alkyl or phenyl. Particularly preferred esters of this type are methoxymethyl, acetoxymethyl, pivaloyloxymethyl, phthalidyl and indanyl. Preparation of these salts and metabolizable esters may be carried out according to conventional procedures for forming salts and esters of beta-lactam antibiotics such as penicillins and cephalosporins.

Preferred compounds of this invention are those wherein m+n equals 3. Also preferred are those compounds wherein X is hydrogen or methyl. Highly preferred compounds are those wherein m+n equals three and X is hydrogen or methyl.

The compounds of this invention possess antibacterial activity as evidenced by their ability to inhibit the growth of microorganisms.

The antibacterial activity of the instant compounds may be determined by testing in standardized in vitro dilution tests for minimum inhibitory concentrations (MICs). Using such standard microbiologic procedures, the 2-(azacycloalkyl)penems of this invention are found to exhibit activity against gram-positive and gram-negative bacteria such as *Staphylococcus aureus*, *Escherichia coli* and *Pseudomonas aeruginosa* at test levels of 0.1 to 100 mcg/ml. Additionally, they show activity against such organisms in the presence of penicillinase and cephalosporinase, indicating a resistance to these enzymes.

As antibacterial agents, the compounds of the present invention are conventionally formulated for oral, parenteral, topical and transdermal use. Thus, the instant invention includes within its scope pharmaceutical compositions comprising the novel compounds of this invention in admixture with a pharmaceutically acceptable carrier therefor. Additionally, the present invention also provides a method of treating bacterial infections in animals, particularly warm-blooded animals, which comprises administering a compound of formula I or a pharmaceutically acceptable salt or metabolizable ester thereof, or a pharmaceutical composition thereof, to an infected host in an amount sufficient to treat such infection.

The dosage administered of the penems of this invention is regulated according to the judgment of the attending clinician depending on such factors as the age and weight of the individual being treated, the mode of administration, and the type and severity of the bacterial infection being prevented or reduced. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

For oral administration, the compounds of this invention are typically formulated in the form of tablets, capsules, elixirs, or the like. For parenteral administration, they may be formulated into solutions or suspensions. Typical topical formulations are those such as lotions, creams, ointments; sprays and mechanical delivery devices, e.g. transdermal.

Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose, and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate; stearic acid vegetable oils such as peanut oil, cottonseed oil, sesame oil, olive oil and corn oil; non-ionic, cationic and anionic surfactants; ethylene glycol polymers; beta-cyclodextrin; fatty alcohols; hydrolyzed cereal solids; water; polyalkylene glycols; isopropanol; gelatin; benzyl alcohol; gums; and petrolatum; as well as ether non-toxic compatible fillers, binders, disintegrants and lubricants commonly used in pharmaceutical formulations. Optionally, the compositions may also contain preservatives, aerosol propellants such as hydrocarbons, and coloring, thickening, suspending, dispersing, emulsifying, wetting, stabilizing and buffering agents. In addition, there may also be included in the composition other active ingredients to provide a broader spectrum of antibacterial activity and/or provide relief of concomitant symptoms such as inflammation.

The compounds of formula I are prepared by reacting an N-oxocarbonyl protected azacycloalkyl acid, a chloroformate agent such as methyl chloroformate and an acid acceptor such as pyridine or triethylamine. The resultant compound is then reacted with a silver salt of an azetidinone represented by formula II.

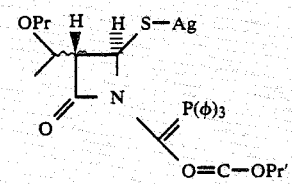

wherein Pr is a removable hydroxy protecting group and Pr' is a removable protecting group.

Suitable Pr hydroxy-protecting groups are those known in the art such as t-butoxycarbonyl, 2,2,2-trichloroethoxycarbonyl, 2-bromoethoxycarbonyl, or paranitrobenzyloxycarbonyl, with 2,2,2-trichloroethoxycarbonyl being preferred for use in this process.

Suitable Pr' protecting groups are those known in the art, preferably one is chosen which can later be removed under the same conditions are Pr. The allyl group is preferred.

The resulting compound is cyclized by heating to reflux in a suitable organic solvent, e.g. benzene, until the cyclization is complete. This usually takes several days.

The protecting groups Pr and Pr' are then removed. The reaction conditions for deprotection depend on the nature of the protecting groups utilized. For example, the 2,2,2-trichloroethoxycarbonyl group is preferably removed by treatment with zinc and glacial acetic at temperatures of from about $-30°$ to about $0°$ C. Groups such as para-nitrobenzyloxycarbonyl are removed by hydrogenolysis, for example, by treating with hydrogen in the presence of a noble metal catalyst such as palladium. The allyl and allyloxycarbonyl groups which are preferred protecting groups used in this invention are preferably removed by utilizing the methods taught in U.S. Pat. No. 4,314,942 to McCombie (1982) which utilizes 2-ethylhexanoic acid or an alkali metal salt thereof and a catalytic amount of an organic soluble palladium complex to effect removal of the protecting groups to give the desired compound of formula I. Additionally, these protecting groups may be removed by the method of Tsuji, Tetrahedron Letters, 7, 613 (1979).

Salts and metabolizable esters of the compounds of this invention may be produced by methods well known in the beta lactam art. For example, salts of the compounds with acid groups can be formed, for example, by treating with metal compounds such as alkali metal salts of suitable carboxylic acids, or with ammonia or a suitable organic amine, wherein preferably stoichiometric amounts or only a small excess of the salt forming agent is used. Acid addition salts of the compounds with basic groupings are obtained in the usual manner, for example, by treating with an acid or a suitable anion exchange reagent. Inner salts of the Zwitterion compounds may be formed by neutralizing salts such as acid addition salts to the isoelectric point. The metabolizable esters can be prepared by reacting the corresponding alkali metal salt of formula I with a chloride of the esterifying group, preferably in a solvent such as dimethylformamide.

The silver salt of formula II can be prepared by converting the azetidinone of formula III

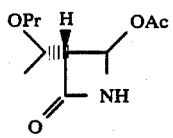

III to a triphenylmethyl thioazetidinone by reacting the compound of formula III with triphenylmethylthiol in the presence of an acid acceptor. Either an inorganic, such as potassium or sodium carbonate, or organic, such as triethylamine, acid acceptor can be used. Typically, the reaction is conducted at temperatures of about 0°–50° C. with room temperatures (about 20°–25° C.) being preferred. The reaction is preferably conducted in an organic solvent such as acetonitrile or pyridine. The reaction takes about 2–24 hours.

The resulting compound is converted to the corresponding phosphorane by reaction with a carboxy-protected 2-hyroxyacetic acid such as a glyoxylic ester or its hemiacetal in an organic solvent such as methylene chloride, chloroform or carbontetrachloride in the presence of a catalytic amount of an acid acceptor such as triethylamine or pyridine at a reaction temperature of preferably room temperature for about five minutes to an hour. The resulting compound is treated with a halogenating agent such as thionyl chloride or thionyl bromide, a mesyl halide such as mesyl chloride or bromide or a phosphorus oxyhalide such as phosphorus oxychloride, in the presence of a basic agent such as an aliphatic tertiary amine, for example, triethylamine, pyridine or collidine, to replace the hydroxy group with chlorine or bromine. The reaction is preferably carried out in the presence of a suitable solvent such as methylene chloride, dioxane or tetrahydrofuran, at temperatures of from about −20° C. to 0° C.

The resulting product is converted to the phosphorane by reaction with a suitable phosphine compound such as a tri-loweralkylphosphine, for example, tri-normalbutylphosphine, or a triarylphosphine, for example, triphenylphosphine. Preferred is the latter compound. The reaction is preferably carried out in the presence of a suitable inert solvent such as dioxane, tetrahydrofuran (THF) or dimethylformamide (DMF). The reaction is preferably conducted at room temperatures.

The resulting product is converted to the silver salt, by reaction with a silver salt such as silver nitrate in a suitable solvent such as methylene chloride, in the presence of a base such as pyridine. The temperature of the reaction is generally cool, e.g. from about −20° C. to about 25° C. The reaction takes about one-half hour.

The following examples describe the preparation of the compounds and compositions illustrative of the present invention.

PREPARATIONS OF INTERMEDIATES (3S,4R,5R)4-acetoxy-3(1-trichloroethoxycarbonyloxyethyl)azetidin-2-one To a solution of 6.2 g methyl (5R,6S,8R)-6-(1-hydroxyethyl)penicillanate in 60 ml. dry methylene chloride at 0° C. under nitrogen was added 3.8 ml pyridine then 3.3 ml β,β,β-trichloroethylchloroformate. The reaction was stirred 15 minutes until all starting material is reacted (as determined by thin layer chromatography with 20% ethyl acetate/chloroform). The solution was poured into 250 ml cold methylene chloride and washed twice with cold 10% phosphoric acid solution, once with cold dilute sodium bicarbonate, and then with water. After drying over anhydrous sulfate, the solvent was removed under vacuum to afford methyl (5R,6S,8R)-6-(1-trichloroethoxycarbonyloxyethyl)-penicillanate.

NMR: $\delta = 5$ 13–5 16 (1H, d); 4.78, (2H, s);

To a solution of mercuric acetate (73.35 g) in glacial acetic acid (500 ml) at 80° C. was added methyl (5R,6S,8R)-6-(1-trichloroethoxycarbonyloxyethyl)-penicillanate (50 g) in small lots. After 2 hours, the mixture was filtered, diluted with ethyl acetate (2 L), washed with water, 10% sodium bicarbonate solution, brine and was then dried and evaporated. The resulting (3S,4R,5R)-1-[(2-methyl-1-methoxycarbonyl)prop-1-enyl]-3-(1-trichloroethoxycarbonyloxyethyl)-4-acetoxyazetidin-2-one was dissolved in acetone (860 ml) and water (70 ml). The solution was stirred and cooled in ice bath while adding potassium pemanganate (23 g). After ½ hour, the solution was diluted with ethylacetate (500 ml) filtered thru celite, concentrated to 300 ml, diluted with an equal volume of ethylacetate and washed several times with water. The organic layer was dried and evaporated to afford the title compound.

NMR: $\delta = 1.42$ (d, J=6 cps), 1.55 (d, J=6 cps), 3.4 (dd, J-2, 8 cps), 4.76 (s), 5.86 (d, J=1.5 cps), 5.90 (d, J=3.0 cps).

B.

(3S,4R,5R)-silver-3-(1'-trichloroethoxycarbonyloxyethyl)-1-(allyl-2''-triphenylphosphoranylidene-2''-acetate)-2-azetidinone-4-thiolate A solution of methyl (5R,6S,8R)-6-(1-hydroxyethyl)-penicillanate (50 g) in acetonitrile (750 ml) was stirred overnight with potassium carbonate (39.6 g) and triphenylmercaptan (59.8 g) under argon. The mixture was filtered and the filtrate was evaporated to dryness. The resulting crude product was chromatographed on silica gel (540 g). Elution with 10% ethylacetate:hexane affords (3S,4R,5R)-3-(1'-trichloroethoxycarbonyloxyethyl)-4-tritylthio-acetidin-2-one.

55 g of (3S,4R,5R)-3-(1'-trichloroethoxycarbonyloxyethyl)4-tritylthio-acetidin-2-one in methylene chloride (600 ml) was treated with allyl glyoxylate allylhemiracetal (17 g) and triethylamine (1.0 g). After stirring for 1 hour the solution was cooled in ice bath, followed by addition of mesylbromide (62.96 g) in one lot and then dropwise addition of a solution of triethylamine (40 g) in methylene chloride (90 ml) while maintaining the reaction temperature below 2° C. After 1 hour, the reaction mixture was filtered through silica gel (300 g) and the eluates with 5% ethylacetate:methylene chloride were collected and evaporated. The resulting bromo intermediate was dissolved in dimethylformamide (300 ml). Triphenylphosphine (30 g) was added and the reaction stirred for 15 hours at room temperature under an argon blanket. The solution was diluted with ethylacetate (500 ml), washed with 10% aqueous sodium bicarbonate, brine, dried over sodium sulfate and evaporated under reduced pressure. The resulting crude product was chromatographed on silica gel (1.5 kg). Elution with 20% ethylacetate:hexane afforded (3S,4R,5R)-3-(1'-trichloroethoxycarbonyloxyethyl)-1-allyl-2''-triphenylphosphoranylidene-2''-acetate)-4-tritylthio-2-azetidinone.

To a mixture of 5.73 g (3S,4R,5R)-3-(1'-trichloroethoxycarbonyloxyethyl)-1-(allyl-2''-triphenylphosphoranylidene-2''-acetate)-4-tritylthio-2-azetidinone in 57 ml methanol was added sufficient methylene chloride to cause solution. The solution was then cooled to 0° C. and 0.92 ml pyridine was added followed by the dropwise addition over a 10 minute period of a solution of 1.37 g silver nitrate in 8 ml water. After five minutes, the reaction mixture was poured over 100 ml ice water. The methylene chloride layer was then separated and the remaining water layer was extracted twice with 50 ml portions of ethyl acetate. The methylene chloride layer and ethyl acetate layers were combined, washed five times with 100 ml portions of cold water and then evaporated to give the title compound.

C. N-allyloxycarbonyl isonipecotic acid

A solution of isonipecotic acid (5.0 g) in 4N sodium hydroxide (9.7 ml) and water (6 ml) was stirred while adding dropwise and simultaneously allylchloroformate (6.0 ml) and 4N sodium hydroxide (16 ml). The reaction mixture was then stirred for 1 hour and washed with ether (50 ml). The aqueous phase was acidified with 1N hydrochloric acid and extracted with ethyl acetate. The organic layers were then washed with water, dried and evaporated to afford the title compound.
M.S.: m/e 213 (M+).

D. By following the procedure described in C above the following N-protected acids are obtained from the corresponding unprotected acids:

N-Allyloxycarbonyl Nipecotic Acid
N-Allyloxycarbonyl Pipecolinic Acid
N-Allyloxycarbonyl D-Proline E.
(4R,3S,5R)-3-(1-trichloroethoxycarbonyloxyethyl)-4-(N-allyloxycarbonyl isonipecotinyl)thio-1-[2″-(allyl 2″-triphenylphosphoranyl acetate)]-azetidin-2-one A solution of N-allyloxycarbonyl isonipecotic acid (1.68 g) in dry tetrahydrofuran (17 ml) containing pyridine (1.27 ml) was cooled to −20° C. and stirred while adding dropwise a solution of methylchloroformate (0.61 ml) in tetrahydrofuran (3 ml) during 7 minutes. The mixture was stirred for 20 minutes. A solution of (3S,4R,5R)-silver-3-(1′-trichloroethoxycarbonyloxyethyl)-1-(allyl-2″-triphenylphosphoranylidene-2″-acetate)-2-azetidinone-4-thiolate (5.5 g) in tetrahydrofuran (20 ml) was then added dropwise to the reaction mixture during 15 minutes. The mixture was stirred at −15° C. for 1 hour and at room temperature for 45 minutes, then diluted with 150 ml ethyl acetate and filtered. The filtrate was washed with brine, dried and evaporated. The crude produce was chromatographed on silica gel (45 g). Elution with 50% ethyl acetate-hexane affords the title compound.
$[\alpha]_D + 17.8°$ (C 0.2, chloroform).

FINAL PRODUCTS

EXAMPLE 1

(5R,6S,8R)
6-(1-hydroxyethyl)-2-(4′-piperidinyl)-2-penem-3-carboxylic acid

A solution of (4R,3S,5R)-3-(1-trichloroethoxycarbonyloxyethyl)-4-(N-allyloxycarbonyl isonipecotinyl)thio-1-[2″-(allyl 2″-triphenylphosphoranyl acetate)]-azetidin-2-one (1.57 g) in benzene (160 ml) was refluxed under nitrogen for 12 days. The solution was then evaporated to dryness and the residue was chromatographed on silica gel (30 g). Elution with 30% ethyl acetate-hexane afforded allyl (5R,6S,8R) 6-(1-trichloroethoxycarbonyloxyethyl)-2-(4′-piperdinyl)-2-penem-3-carboxylate.
$[\alpha]_D + 103.8°$ (C 0.8, chloroform); M.S. m/e 596;
NMR: $\delta = 1.50$ (d, 3H, J=6 cps), 3.86 (dd, 1H, J=2,7 cps), 4.77 (S, 2H), 5.55 (d, 1H, J=2 cps).

0.27 g of allyl (5R,6S,8R), 6-(1-trichloroethoxycarbonyloxyethyl)-2-(4′-piperdinyl)-2-penem-3-carboxylate was dissolved in tetrahydrofuran (3 ml) containing glacial acetic acid (0.85 ml) and water (0.85 ml). The solution was cooled to −15° C. and zinc dust (0.25 g) was added in small lots during 2 hours while the mixture was stirred vigorously. After a further 30 minutes the mixture was filtered, the filtrate was diluted with brine and extracted with ethyl acetate. The extract was then washed with 5% aqueous sodium bicarbonate, brine, dried and evaporated under reduced pressure. The residue was chromatographed on silica gel (2 g). Elution with chloroform afforded allyl (5R,6S,8R) 6-(1-hydroxyethyl)2-(4′-piperidinyl)2-penem-3-carboxylate.
$[\alpha]_D$ 103° (C 2.0, chloroform); M.S.: m/e 422;
NMR: $\delta = 1.34$ (d, 3H, J=6 cps), 1.46 (m, 4H), 2.26 (m, 1H) 3.69 (dd, 1H, J=2,7 cps), 5.56 (d, 1H, J=2 cps)

0.06 g of a solution of allyl (5R,6S,8R)-6-(1-hydroxyethyl)-2-(4′-piperidinyl)-2-penem-3-carboxylate in methylene chloride (0.6 ml) containing tetrakis (triphenylphosphine) palladium (0.025 g), triphenylphosphine (0.04 g) and 1M 2-ethylhexanoic acid in methylene chloride (0.32 ml) was stirred under nitrogen. A precipitate appeared after a few minutes. The mixture was stirred for 1 hr. and then shaken with distilled water (10 ml). The aqueous layer was washed several times with chloroform and then lyophylized to afford the title compound
$[\alpha]_D + 96.8°$ (C 0.23, water); IR 5.65;
NMR: $\delta = 1.3$ (d, 3H, J=6 cps), 1.82 (m, 4H), 3.83 (dd, 1H, J=1.7, 7 cps), 5.61 (d, 1H, J=1.7 cps).

EXAMPLE 2

(5R,6S,8R,3′RS)
6-(1-hydroxyethyl)-2-(3′-piperidinyl)-2-penem-3-carboxylic acid

Following the procedures described in Preparations C, D and E and in Example 1 and using N-allyloxy carbonyl nipecotic acid as a reactant in the title compound is obtained.

EXAMPLE 3

(5R,6S,8R,2′RS)
6-(1-hydroxyethyl)-2-(2′-piperidinyl)-2-penem-3-carboxylic acid

Following the procedures described in Preparations C, D and E and in Example 1, and using N-allyloxycarbonyl pipecolinic acid as a reactant the title compound was obtained.
IR: 5.65μ.

EXAMPLE 4

(5R,6S,8R,2′R)
6-(1-hydroxyethyl)-2-(2′pyrrolidinyl)-2-penem-3-carboxylic acid

Following the procedures described in Preparation C, D and E and in Example 1 and using N-allyloxycarbonyl D-Proline as a reactant the title compound was obtained.
IR: 5.65μ.

EXAMPLE 5

(5R,6S,8R) 6-(1-hydroxyethyl)-2-(N-acetimidoyl 4'-piperdinyl)-2-penem-3-carboxylic acid A solution of the title compound of Example 1 (0.1 g) in water (1 ml) containing sodium bicarbonate (0.09 g) was treated with ethylacetimidate (0.2 g). The solution was stirred for 30 minutes and then chromatographed on Dowex 50×4. Elution with water followed by lyophilization of the eluates afforded the title compound.
IR: 5.65μ.

EXAMPLE 6

(5R,6S,8R) 6-(1-hydroxyethyl)-2-(N-amidino 4'-piperidinyl)-2-penem-3-carboxylic acid A solution of the title compound of Example 1 (0.1 g) in water (1 ml) containing sodium bicarbonate (0.15 g) was stirred with S-benzylthiourea hydrochloride (0.2 g) for an hour. The title compound was isolated by reverse phase HPLC.
IR: 5.65μ.

Following the procedures of the foregoing Examples and Intermediate preparations, and utilizing as intermediates, the corresponding azacycloalkyl compounds, the following compounds of formula I can be made.

[Structural formula diagram]

| Stereochemical configuration | (substituent) |
|---|---|
| 5R,6S,8R | 3'-pyrrolidinyl |
| 5R,6S,8R,2'R | 4'-hydroxy-2'-pyrrolidinyl |
| 5R,6S,8R,2'R | 2'-azacycloheptyl |
| 5R,6S,8R | 3'-azacycloheptyl |
| 5R,6S,8R | 4'-azacycloheptyl |
| 5R,6S,8R,2'R | 2'-azacyclooctyl |
| 5R,6S,8R | 3'-azacyclooctyl |
| 5R,6S,8R | 4'-azacyclooctyl |
| 5R,6S,8R | 5'-azacyclooctyl |
| 5R,6S,8R,2'R,6'R | 2'-carboxy-6'-piperidinyl |
| 5R,6S,8R,2'R | 2'-carboxy-5'-piperidinyl |
| 5R,6S,8R,2'R | 2'-carboxy-4'-piperidinyl |
| 5R,6S,8R,2'R,7'R | 2'-carboxy-7'-azacycloheptyl |
| 5R,6S,8R,2'R | 2'-carboxy-6'-azacycloheptyl |
| 5R,6S,8R,2'R | 2'-carboxy-5'-azacycloheptyl |
| 5R,6S,8R,2'R,8'R | 2'-carboxy-8'-azacycloheptyl |
| 5R,6S,8R,2'R | 2'-carboxy-7'-azacyclooctyl |
| 5R,6S,8R,2'R | 2'-carboxy-6'-azacyclooctyl |
| 5R,6S,8R,2'R | 2'-carboxy-5'-azacyclooctyl |
| 5R,6S,8R,2'R | 5'-methylthio-2'-piperidinyl |
| 5R,6S,8R,2'R | 5'-hydroxy-2'-piperidinyl |
| 5R,6S,8R,2'R | 6'-methylthio-2'-azacycloheptyl |
| 5R,6S,8R,2'R | 6'-hydroxy-2'-azacycloheptyl |
| 5R,6S,8R,2'R | 7'-methylthio-2'-azacyclooctyl |
| 5R,6S,8R,2'R | 7'-hydroxy-2'-azacyclooctyl |
| 5R,6S,8R,2'R | 3'-carboxy-2'-azacyclobutyl |
| 5R,6S,8R,2'R,4'R | 4'-carboxy-2'-azacyclobutyl |
| 5R,6S,8R,2'R | 3'-methylthio-2'-azacyclobutyl |
| 5R,6S,8R,2'R | 3'-hydroxy-2'-azacyclobutyl |

The following are typical pharmaceutical formulations containing as the active ingredient, the compounds of this invention. The active ingredient may be (5R,6S,8R) 6-(1-hydroxyethyl)-2-(4'-piperidinyl)-2-penem-3-carboxylic acid; (5R,6S,8R,3'RS) 6-(1-hydroxyethyl)-2-(3'-piperidinyl)-2-penem-3-carboxylic acid; (5R,6S,8R,2'RS) 6-(1-hydroxyethyl)-2-(2'-piperidinyl)-2-penem-3-carboxylic acid; (5R,6S,8R,2'R) 6-(1-hydroxyethyl)-2-(2'-pyrrolidinyl)-2-penem-3-carboxylic acid; (5R,6S,8R) 6-(1-hydroxyethyl)-2-(N-acetimidoyl 4'-piperidinyl)-2-penem-3-carboxylic acid or (5R,6S,8R) 6-(1-hydroxyethyl)-2-(N-amidino 4'-piperidinyl)-2-penem-3-carboxylic acid or an equivalent amount of any of the other compounds of this invention.

FORMULATION 1

Capsules

| No. | Ingredient | mg/capsule | mg/capsule |
|---|---|---|---|
| 1. | Active ingredient | 250 | 500 |
| 2. | Lactose USP | 100 | 50 |
| 3. | Corn Starch, Food Grade | 50 | 43.5 |
| 4. | Microcrystalline Cellulose NF | 95 | 50 |
| 5. | Magnesium Stearate NF | 5 | 6.5 |
|  | Total | 500 | 650 |

Method of Manufacture

Mix Items Nos. 1, 2, 3 and 4 in a suitable mixer for 10–15 minutes. Add Item No. 5 and mix for 1–3 minutes. Fill the mixture into suitable two-piece hard gelatin capsules using encapsulating machine.

FORMULATION 2

Tablets

| No. | Ingredient | mg/tablet | mg/tablet |
|---|---|---|---|
| 1. | Active ingredient | 250 | 500 |
| 2. | Lactose USP | 57 | 114 |
| 3. | Corn Starch, Food Grade, as a 10% paste in Purified Water | 20 | 40 |
| 4. | Corn Starch, Food Grade | 18 | 39 |
| 5. | Magnesium Stearate NF | 5 | 7 |
|  | Total | 350 | 700 |

Method of Manufacture

Mix Item Nos. 1 and 2 in a suitable mixer for 10–15 minutes. Granulate the mixture with Item No. 3. Past the wet granulation through a coarse screen (e.g., ¼") if needed, and dry the wet granules. Mill the dried granules. Combine Item No. 4 and the dried granules and mix for 10–15 minutes. Add Item No. 5 and mix for 1–3 minutes. Compress the mixture to appropriate size and weight on a suitable tablet machine.

FORMULATION 3

Injectable Powder: (per vial)

|  | g/vial | g/vial |
|---|---|---|
| Active Ingredient | 0.5 | 1.0 |

Add sterile water for injection or bacteriostatic water for injection for reconstitution.

FORMULATION 4

Injectable Solution

| Ingredient | mg/ml | mg/ml |
|---|---|---|
| Active Ingredient | 100 | 500 |
| Methylparaben | 1.8 | 1.8 |

-continued

| Ingredient | mg/ml | mg/ml |
|---|---|---|
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture
1. Dissolve parabens in a portion (85% of the final volume) of the water for injection at 65°–70° C.
2. Cool to 25.35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22μ membrane and fill into appropriate containers.
6. Terminally sterilize the units by autoclaving.

FORMULATION 5

Injectable Powder: (per vial)

|  | g/vial |
|---|---|
| Active Ingredient | 1.0 |
| Sodium Citrate | 0.05 | pH is adjusted to 6.2 using 0.1N citric acid solution.

Add sterile water for injection or bacteriostatic water for injection for reconstitution.

What is claimed is:

1. A compound of the formula:

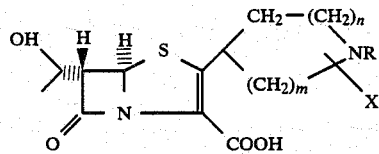

wherein
m is 0–2;
n is 1–3; and
X is a hydrogen, lower alkyl, lower alkoxy, amino, hydroxy, lower alkylthio, or carboxy group;
R is amidino or

wherein R' is hydrogen or $C_1$–$C_3$ alkyl;
or a pharmaceutically acceptable salt or a metabolizable ester thereof, in racemic or optically active form.

2. A compound according to claim 1 wherein R is acetimidoyl or amidino.

3. A compound according to claim 1 wherein m+n equals 3.

4. A compound according to claim 3 wherein X is hydrogen or methyl.

5. A compound according to claim 1 which is (5R,6S,8R) 6-(1-hydroxyethyl)-2-(N-acetimidoyl-4'-piperdinyl)-2-penem-3-carboxylic acid.

6. A compound according to claim 1 which is (5R,6S,8R) 6-(1-hydroxyethyl)-2-(N-amidino-4'-piperidinyl)-2-penem-3-carboxylic acid.

7. A pharmaceutical composition comprising an effective amount of an antibacterial compound of claim 1 in admixture with a pharmaceutically acceptable carrier therefor.

8. A composition according to claim 7 wherein said antibacterial compound is (5R,6S,8R) 6-(1-hydroxyethyl)-2-(N-acetimidoyl-4'-piperdinyl)-2-penem-3-carboxylic acid.

9. A composition according to claim 7 wherein said antibacterial compound is (5R,6S,8R) 6-(1-hydroxyethyl)-2-(N-amidino-4'-piperidinyl)-2-penem-3-carboxylic acid.

10. A composition according to claim 7 adapted for oral administration.

11. A composition according to claim 7 adapted for parenteral administration.

12. A method of preventing bacterial infections in warm-blooded animals in need of said treatment which comprises administering thereto an antibacterial effective amount of a compound of claim 1.

* * * * *